United States Patent [19]
Lloyd et al.

[11] 4,421,665
[45] Dec. 20, 1983

[54] CONTACT LENS CLEANING COMPOSITION CONTAINING LIPID SOLVENT AND METHOD OF USING

[76] Inventors: Eugene A. Lloyd, 116 Broadway; Peter Madri, 33 S. Bay Ave., both of Amityville, N.Y. 11701; William J. Closson, 179 Jayne Ave., Patchogue, N.Y. 11772

[21] Appl. No.: 226,155

[22] Filed: Jan. 19, 1981

Related U.S. Application Data

[63] Continuation-in-part of Ser. No. 181,164, Aug. 25, 1980, abandoned.

[51] Int. Cl.$^3$ .............. C11D 3/43; C11D 3/44; C11D 3/48; C11D 7/50
[52] U.S. Cl. .................... 252/106; 134/40; 134/42; 252/162; 252/170; 252/171; 252/172; 252/173; 252/174.21; 252/DIG. 10; 252/DIG. 14
[58] Field of Search .............. 134/40, 42; 252/106, 252/162, 170, 171, 172, DIG. 10, 107

[56] References Cited

U.S. PATENT DOCUMENTS

| | | | |
|---|---|---|---|
| 2,748,084 | 5/1956 | De Lew | 252/172 |
| 3,737,386 | 6/1973 | Geiss | 252/162 |
| 4,046,706 | 9/1977 | Krezanoski | 252/106 |
| 4,104,187 | 8/1978 | Sibley | 252/106 |
| 4,126,587 | 11/1978 | Sibley | 252/541 |
| 4,127,423 | 11/1978 | Rankin | 134/30 |

OTHER PUBLICATIONS

Mellan, *Industrial Solvents*, Reinhold Publishing Corp., New York, 1950, pp. 286, 315, 318.
Handbook of Chemistry & Physics, 44th Ed., The Chemical Rubber Publishing Co., Cleveland, Ohio, 1961, p. 2632.

*Primary Examiner*—Dennis L. Albrecht
*Attorney, Agent, or Firm*—Posnack, Roberts, Cohen & Spiecens

[57] ABSTRACT

A composition for cleaning lenses which includes a non-polar solvent in the form of cyclohexane and/or ethyl acetate with a trace amount of an organic solvent in the form of chloroform or ethyl acetate and a polar solvent in the form of an alcohol. The composition further includes thimerosal, a wetting agent, a surfactant, and a buffer. The composition is provided as a saline solution.

43 Claims, 5 Drawing Figures

CONTACT LENS CLEANING COMPOSITION CONTAINING LIPID SOLVENT AND METHOD OF USING

OTHER APPLICATIONS

This application is a continuation-in-part of our earlier filed copending application, Ser. No. 181,164 filed Aug. 25, 1980 (now abandoned).

FIELD OF INVENTION

This invention relates to compositions and methods for the cleaning, wetting and asceptizing of various types of contact lenses, including but not limited to P.M.M.A. lenses, P.M.M.A. component lenses, C.A.B. lenses, C.A.B. component lenses, soft lenses, and silicone and silicone derivative lenses as discussed in greater detail hereinbelow.

BACKGROUND

Various kinds of contact lenses have been developed for applying visual corrections to the human eye. Some of the types of contact lenses which are presently available commercially have been mentioned hereinabove.

It is known, for example, that hard contact lenses are made of polymethylmethacrylate materials. Proper care of such lenses, for example, had included storing the same in specially developed cleaning and storage solutions to maintain them in suitable condition when not in use. The storage solutions are furthermore generally used to sterilize the lenses during storage. When ready for use, hard contact lenses are immersed into wetting solutions designed to condition and prepare the same for wetting by natural tear fluids in order to make the wearing of the contact lenses more tolerable by reducing irritation of the eye. Prior art contact lens wetting solutions have frequently contained polyvinyl alcohol as a wetting agent.

Another type of contact lens which has been developed is the gas-permeable cellulose acetate butyrate lens. Lenses of this type are somewhat more flexible than the hard polymethylmethacrylate lenses, but are less flexible than the well-known soft lenses. Cellulose acetate butyrate lenses are based on organic cellulose esters produced by a reaction between cellulose and the appropriate acid and anhydrides in the presence of a suitable catalyst. For example, cellulose acetate may be esterified with a mixture of butyric acid, acidic anhydride, and concentrated sulfuric acid catalyst.

The development of flexible lenses has been generally considered in two broad categories, namely, hydrophilic and hydrophobic lenses. Hydrophobic contact lenses are usually based on elastic and flexible silicone rubber (polysiloxane) and are generally made of cross-linked dimethyl polysiloxane. A typical lens of this type is disclosed in U.S. Pat. No. 3,228,741. Hydrophilic soft contact lenses include hydrated gel lenses, which can be prepared, for example, by copolymerizing hydrophilic, organic monomers having an olefinic double bond with a small amount of cross-linking agents usually having two polymerizable olefinic double bonds. These lenses may usually be based on polyhydroxylated alkyl methacrylates cross-linked, for example, with a hydroxyethyl dimethacrylate. Hydrated gel lenses may, for example, include hydroxyethyl methacrylate or its analogs, ethylene-glycol dimethacrylate or its analog, polymethylmethacrylate or its analog, polyvinyl pyrrolidone, and so forth. Hydrated gel lenses are disclosed, for example, in U.S. Pat. Nos. 3,220,960; 3,361,858; and 3,499,862.

Silicone and silicone derivative lenses may for example be prepared of hydroxy dimethyl silane. This type of lens and the other lenses mentioned above as well as various other types of lenses which have been developed are all cleanable and wettable by the compositions set forth herein as will be discussed in greater detail hereinbelow. As will also be shown below, the elements of the composition of the invention synergistically cooperate with one another in a manner not known in the prior art, which is exemplified in a broad collection of patents including but not limited to U.S. Pat. Nos. 2,386,106; 3,240,709; 3,431,343; 3,882,036; 3,888,782; 3,954,644; 4,046,706; 4,013,576; 4,104,187; and 4,127,423.

In U.S. Pat. No. 2,386,106, Wilmer Gangloff discloses a detergent for cleaning hard, polished glass surfaces. This patent discloses that a dihydric alcohol, 2-methyl-2,4-pentane diol when added to water in varying percentages, not only lowers the surface tension of water but provides a detergent composition which is sutable for cleaning hard, polished glass surfaces.

Billy Rankin discloses in U.S. Pat. No. 3,240,709 a cleaning composition for contact lenses and like ophthalmic apparatus. This patentee more particularly discloses a cleaning composition comprised of wetting agents which readily dissolve crystalline tear deposits without harming the contact lens ingredients. The cleaning composition disclosed is buffered to the pH range of the human tear. A principal ingredient of the cleansing solution is methylcellulose which is of 4,000 centipoises which has a good ability to lower the surface tension and is non-reactant with conventional ophthalmic buffering agents.

Herbert Stecker in U.S. Pat. No. 3,431,343 discloses a method of obtaining germicidal and fungicidal activities by contacting microorganisms with an effective concentration of a compound having the general formula:

wherein: X is a halogen atom of the class consisting of chlorine and fluorine; Y is a member of the class consisting of hydrogen, methyl, bromine and chlorine; and n is a numeral from 0 to 3.

Examples of the Stecker composition include: 2,2'-trifluoromethyl-methylene-bisphenol; 2,2'-dichloromonofluoromethyl methylene-bisphenol; 2,2'-difluoromonochloro-bis (4,6-dichlorophenol); 2,2'-trifluoromethyl-methylene-bis (3,4,6-trichlorophenol); and 2,2'-trifluoromethyl-methylene-bis (4,6-chloro-5-methyl phenol).

In U.S. Pat. No. 3,882,036 is disclosed a contact lens cleaning, storing, and wetting solution especially adapted for flexible silicone contact lenses. The solution comprises a poly-(oxyethylene)-poly(oxypropylene) block copolymer having a molecular weight between about 1,900 and 15,500, a water solubility in excess of about 10 grams per 100 ml., a cloud point in 1% aqueous solution above about 30° C., a microbial growth inhibitor, purified water, and a neutral water-soluble compatible salt to provide a specified salt content. The patentees Joseph Krezanoski et al further disclose that the solution can contain disodium or trisodium ethylenediamine, tetraacetate and a polymeric viscosity building agent.

M. Boghosian, in U.S. Pat. No. 3,888,782, discloses an aqueous substantially isotonic cleaning and sterilizing solution for plastic hydrophilic soft contact lenses including chlorhexidine and polyvinylpyrrolidone. It is alleged that the sterilizing solution is non-toxic to the eye of the wearer and in the presence of a suitable amount of water-soluble polyhydroxyethylmethacrylate prevents the build-up of opaque deposits on the surface of soft contact lenses.

J. Krezanoski et al make a further disclosure of a contact lens cleaning, storing and wetting solution in U.S. Pat. No. 3,954,644.

J. Krezanoski, in U.S. Pat. No. 4,046,706 discloses a composition for cleaning contact lenses which comprises poly(oxyethylene)-poly(oxypropylene) block copolymer having a molecular weight as mentioned hereinabove with other characteristics corresponding to the previously indicated Krezanoski patents.

S. Loshaek discloses in U.S. Pat. No. 4,013,576 a contact lens treating composition resulting from the incorporation of an amphoteric surfactant as a detergent, which provides good cleaning properties with no eye irritation and is stable in the presence of positively charged bacteriocides in the composition.

Murray Sibley et al disclose in U.S. Pat. No. 4,104,187 methods and compositions for the elevated temperature disinfection of soft contact lenses. Attention is called, by way of example, to the use of an aqueous stabilized saline solution having a small amount of non-irritating neutral surfactants. It is pointed out that a particularly effective surfactant is N-hydroxyalkylated fatty acid amides.

In U.S. Pat. No. 4,127,423, Billy Rankin discloses that silicone and hydrophilic soft contact lenses may be freed of proteinaceous deposits and other deposits by rubbing them with an aqueous solution of a crystalline sodium silicate having a pH of 10.2–10.9 and rinsing the same. It is pointed out that the solution may contain, in addition, sodium chloride in isotonic amounts, viscosity agents, wetting agents, detergents and bacteriocides.

While some of the patents suggest various features in common with the disclosure to follow hereinafter, it will become obvious that the above patents do not disclose certain of the elements to be mentioned hereinbelow nor the synergistic effect of such elements in combination with various other constituents of the compositions to be mentioned hereinbelow. It will also become obvious that the compositions and methods disclosed hereinbelow represent a significant advancement in the art of contact lens cleaning.

Examples of antimicrobials/preservatives used either in contact lens solutions or in "ophthalmologicals" include CHLOROBUTANOL which the *Merck Index* calls "Acetone Chloroform." Its structure is:

It is described as an antiseptic and preservative for biological fluids. It is currently used in an anti-glaucoma drug called phospholine iodide, produced by Ayerst. It is not known to have lens cleaning properties.

Finally, in the article "Microbiology of Soft and Hard Contact Lens Care" which comes from *Symposium on Flexible Contact Lenses,* ed. J. Bitonte and G. Feldman (C. V. Mosby, 1972), pages 211 and 212, it can be seen that under specified test conditions, thimerosal cannot eliminate *Staphylococcus aureus* (or Micrococcus or Bacillus) even after prolonged soaking. Thimerosal is not very active against "Gram Positive" microorganisms but is very active against "Gram Negative" organisms.

SUMMARY OF INVENTION

It is an object of the invention to provide improved methods and compositions for the cleaning and wetting of contact lenses in a form superior to those disclosed by any of the patents mentioned hereinabove or indeed any of the prior art available in related fields at the present.

It is a further object of the invention to provide improved cleaning and wetting solutions suitable for use in vitro and/or in vivo contact lens cleaning and preparation.

It is yet another object of the invention to provide an improved product and method suitable for the cleaning and maintenance of all commonly used contact lenses available at the present time such as, for example, P.M.M.A., P.M.M.A. component lenses, C.A.B. lenses, C.A.B. component lenses, soft lenses, silicone and silicone derivative lenses and the like.

Yet another object of the invention is to provide for the cleaning and wetting of all known contact lens materials and particularly methods and compositions which will substantially and effectively kill all pathogenic bacteria, fungi, and viruses associated with eye pathology within a six-hour period using, for example, as a test basis an initial inoculum of $10^5$ organisms/ml final concentration.

It is still another object of the invention to provide improved methods and compositions to eliminate the use of chlorhexidine and acetate disodium as microbiocidals.

As has been indicated hereinabove, it is still another object of the invention to provide improved methods and compositions which will allow in cases of hard, soft or silicone contact lenses or the like the cleaning of such lenses in vivo.

Still a further object of the invention is to provide improved methods and compositions which permit a complete cleaning of silicone lenses which have been until the present extremely difficult or impossible to clean after extended periods of time.

Another object of the invention is to provide improved methods and compositions serving as ocular decongestants.

As will be seen hereinafter, it is a further object of the invention to provide improved methods and compositions permitting use of cyclohexane as a mucolipid reducer and in conjunction with other additives as a bactericidal solution.

Yet another object of the invention is to provide an improved hypo-allergenic technique and to provide for increasing the wetting angle of all contact lenses, thereby allowing a greater tear flow barrier and insuring increased wear time.

In achieving the above and other objects of the invention, there is provided a composition for cleaning lenses comprising a non-polar solvent adapted to provide for enhanced solubility of lipids and lipoproteins. More specifically, while other non-polar solvents are available, the preferred non-polar solvent in accordance with the invention is cyclohexane or ethyl acetate which have been found to be physiologically adaptable to the human eye. Preferably, the cyclohexane is present in the composition in an amount of about 0.001 to 1.0% by volume. The composition of the invention may further include another organic or non-polar solvent such as chloroform or ethyl acetate which, if not already present as a non-polar solvent, may be present in trace amounts (0.0001 to 0.01% or 0.0001 to 1%, respectively) and the composition is, further, preferably in the form of a saline solution where, for example, the saline is 0.85-0.95 weight percent of NaCl.

In accordance with other features of the invention, there is incorporated in the composition of the invention at least one alcohol, the significance of which will be clarified hereunder. This alcohol may preferably be ethanol.

In further accordance with the invention, the solution will furthermore include a wetting agent present preferably in the solution in an amount of 0.05 to 10% by weight. This wetting agent may, for example, be polyvinyl alcohol, which is a preferred wetting agent.

In accordance with still further features of the invention, the solution may include from about 0.0005-0.7% by weight of thimerosal. The thimerosal may thus, for example, be present in an amount of 0.004% by weight. The use of thimerosal in contact lens composition is known. The use of other antimicrobial agents alone or in combination with thimerosal, such as chlorobutanol, chlorhexidine, sodium edetate, sorbic acid, phenylethylalcohol, etc., may also be considered appropriate for this solution. The effect of the thimerosal is greatly improved in accordance with the invention as will be seen in greater detail hereinafter.

The composition of the invention may furthermore comprise a surfactant. This surfactant will be present in an amount of about 0.001-10% by weight. An example of such a surfactant is octylphenoxypolyethoxyethanol. The surfactant may also be various salts of fatty acids or the like.

In addition to or included with the aforementioned constituents, the solution may furthermore include a buffer to adjust the pH range of the solution to about 5-10. The buffer may, for example, be a sodium and/or potassium phosphate, borate or citrate. Various compatible glycols may also be used as buffers.

According to the method of the invention, the composition or various portions thereof are applied to contact lenses in various ways. Thus, for example, where a lens is fabricated of polymethylmethacrylate or an analog thereof, the method may comprise soaking the lens in the composition of the invention before the initial use of the lens. Thereafter, the lens will be rinsed with water and an additional amount of the composition will be applied to the lens which will then be rubbed between the fingers. The lens is then dried with a lint-free material such as, for example, Kleenex TM, and more of the mixture is applied to the lens whereafter the lens is inserted onto the eye of the user.

Where the lens is, for example, of hydroxymethylmethacrylate or an analog thereof, the method may comprise supplying a part of the composition to the lens and allowing the lens to stand for at least one minute before being placed onto the eye of the user and then applying a drop of the composition of the invention to the inner lower lid of the user.

Where the lens is, for example, of silicone or a silicone derivative, the method may comprise soaking the lens in the composition of the invention for at least ten hours before the initial use, rinsing the lens with water, applying further of the composition to the lens and inserting the same onto an eye of the user and applying a further part of the solution to the inner lower lid of the user.

The above objects, features, and advantages of the invention will be found in the detailed description which follows hereinbelow as illustrated in the accompanying drawing.

DETAILED DESCRIPTION

It is theorized that lipids, lipoproteins and proteins become attached to the contact lens because of surface charges produced on the contact lens surface when the eyelid sweeps across the contact lens in the normal blinking process. This surface charge attracts portions of the above-mentioned molecules of the opposite charge. Once an initial layer of these molecules is deposited, it facilitates deposition of similar molecules on top owing to the polarity of minor structures in all of the above-mentioned molecules.

Lipids and lipoproteins are only slightly soluble in aqueous solutions, but dissolve readily in non-polar solvents. Some examples of such solvents are cyclohexane ($C_6H_{12}$), chloroform ($CHCl_3$), petroleum ether ($C_2H_5OC_2H_5$), hexane ($CH_3(CH_4)_4CH_3$), and benzene ($C_6H_6$). These solubility characteristics stem from the rather large hydrocarbon portion of the lipid molecule. When lipids are in combination with a protein molecule they are slightly soluble in aqueous solutions but are significantly more soluble in a solvent that has both polar and non-polar aspects. Such a solution can be a mixture of water and a non-polar solvent. The most complete extraction of lipids occurs with a mixture of alcohol and cyclohexane, chloroform or ether. An example of another organic solvent which may be used is ethyl acetate ($CH_3COOC_2H_5$). The applicability of this solvent is due to its ability to solubilize the physiological substances including proteins, lipoproteins and lipids which may contaminate lens surfaces. Thus, while other non-polar solvents exist, only cyclohexane and ethyl acetate meet the requirements and limitations of this invention.

A surfactant has the ability to solubilize lipids in an aqueous medium. It does this because of its inherent polar-non-polar structure. The non-polar lipid is actually soluble in the non-polar portion of the surfactant and the surfactant, in turn, is soluble in the polar aqueous medium because of its polar groups. In this process, micelles are formed and the lipid is removed from the vicinity of the contact lens by the aqueous tear production.

According to the invention, the non-polar solvent employed in accordance therewith is preferably cyclohexane and/or ethyl acetate and the composition of the invention comprises generally:

0.001–1.0% by volume of said cyclohexane or said ethyl acetate or mixtures thereof (as the non-polar solvent)

0.1–10% by volume of said ethanol 0.0001–0.01% by volume of chloroform or ethyl acetate (as a further organic solvent)

q.s. to 100% by volume of normal saline 0.0001–10% by weight of a physiologically acceptable surfactant 0.05–10% by weight of a physiologically acceptable wetting agent 0.05–1.0% by weight of a buffer 0.001–0.6% by weight of thimerosal

Examples of the above will be given hereinbelow.

Preparation of the composition of the invention involves generally the following: to 0.1–10% by volume of an alcohol such as ethanol is added the cyclohexane and/or ethyl acetate employed in accordance with the invention. Preferably the alcohol is employed in an amount of 0.1–1.2% by weight. Ethanol is representative of an alcohol and is the preferred alcohol which is employed.

The lower level of the cyclohexane or ethyl acetate which is mentioned above is 0.001% by volume. The cyclohexane does substantial effective work at this lower level. Some work as a bacteriostatic agent will be done below this level, and if a lower effectiveness can be tolerated, a yet lower limit can be employed in accordance with the invention. The specified practical upper limit of the cyclohexane or ethyl acetate is 1.0%. Preferably the cyclohexane is employed in an amount of 0.01–0.2% by volume.

To the mixture of alcohol and ethyl acetate or cyclohexane may be added a trace amount of chloroform preferably in the range of 0.0001 to 0.01% by volume. Ethyl acetate in the range of 0.0001% to 1.0% may be used rather than chloroform. To this mixture is added normal saline in an amount to bring the composition to 100% by volume. The saline is, for example, 0.85–0.95 weight percent of NaCl. Potassium chloride may also be employed; any salt may be employed which gives the desired tonicity. The solution should be isotonic or slightly hypertonic relative to the human tear solution, thereby relating to a 7.1–7.4 pH.

To the aforesaid solution is added a wetting agent such as, for example, polyvinyl alcohol, the formula for which is Other wetting agents may alternatively be employed. Thus, for example, methylcellulose or hydroxypropylmethylcellulose or dextran or polyethyleneglycol homopolymers may be employed. The function of this constituent of the composition is to act as a wetting agent and comfort drop. It is preferably employed in an amount of 0.05–10% by weight.

To the solution thusly prepared is added a surfactant. This, for example, may be octylphenoxypolyethoxyethanol. Various salts of fatty acids such as dioctylsulfosuccinate may also be employed. The surfactant is preferably added in an amount of 0.0001–10% by weight. Preferably, the surfactant is used in an amount of about 0.001% by weight.

In accordance with the invention, use of non-ionic surfactants is preferred for various reasons. The non-ionic nature of the surfactant is preferred to lessen the possibility of surface charges developing on the contact lens and to maintain the pH of the solution in the desired range. Some examples of other non-ionic surfactants are as follows: (1) LUBROL WX (fatty alcohol ethoxylate); (2) MYRJ 59 (Polyethylene stearate); and (3) TWEEN-20 (Polyoxyethylene sorbitan monolaurate).

Before the octylphenoxyethanol or other such surfactant is added, thimerosal is added to the solution. This is added generally in a range of 0.001–0.6% by weight and is preferably added in an amount of 0.004% by weight. Thimerosal is identified as [(o-Carboxyphenyl)thio] ethylmercury sodium salt. The suitability of thimerosal as a preservative in soft lens soaking solutions is discussed by S. Eriksen, et al in *Symposium on Flexible Contact Lenses*, ed. J. Bitonte and G. Feldman (C. V. Mosby, 1972). As will be discussed hereinafter, the utility of thimerosal is known. However, its usefulness is greatly enhanced in accordance with the principles of the invention as will become hereinafter apparent.

Generally, it will be noted that the composition of the invention should be stored in bottles of relatively small capacity such as, for example, three or four fluid ounces. However, a wide range in the bottle capacity is permissible and the indication of three or four fluid ounces is given by way of preference and not of limitation. The bottle should be kept tightly capped when not in use. The orifice of the bottle should be relatively small as is consistent with conventional bottles now in commercial use. The orifice should be of such shape as to permit dispensing of the composition of the invention directly into the eye of the user such as in placing drops within the inner lower lid of a user. Preferably, the storage and dispensing bottle employed to accommodate the composition of the invention should be kept in the dark. The solution should be kept relatively cool and should not be permitted to become overheated.

As for conditions of use, there are no special conditions for use. The composition might be gently agitated and as is conventional, the dropper or storage bottle should not be permitted to touch the surface of the eye when placing drops in the eye or on the lid of the user.

There are various techniques for use of the composition of the invention. When P.M.M.A. lenses or P.M.M.A. component lenses are utilized, the new lenses should be soaked from one to four hours prior to initial use and thereafter rinsed with water or the like. The composition of the invention should then again be applied to the lens which should then be rubbed between the fingers. Thereafter, the lens can be dried with a lint-free material such as, for example, Kleenex ™. Further solution or composition is applied to the lens which may then be placed directly onto the eye of the user.

In the event that C.A.B. or C.A.B. component lenses are employed, it is preferred that these lenses be soaked for 24 hours before initial use. Such a lens may then be rinsed in water or the like whereafter solution or composition is supplied to the lens which is rubber between the fingers. The lens is dried with a lint-free material such as Kleenex TM, and the lens is then covered with solution and placed directly on the eye of the user.

In the case of soft lenses such as those fabricated of hydroxymethyl methacrylate, the new lens may be placed on the palm of the hand of the user and composition applied to the lens. The lens is allowed to stand for approximately one minute and, after it is made certain that the lens is free from all foreign bodies, the lens can be placed on the eye whereafter one drop of the composition of the invention is applied to the inner lower lid of the user while he is wearing the lens.

For silicone and silicone derivative lenses, the new lens is placed into solution for at least 10 hours before initial use whereafter it is rubbed between the fingers and rinsed with warm water. The solution is then applied to the lens which is placed on the eye. Thereafter, one drop of the composition of the invention is applied to the inner lower lid of the user and the solution can then be applied directly to the eye or lens as required. Cleaning protocols are not necessarily limited to those described above and may vary according to particular needs, although the above protocols are preferred.

For purposes of testing cleaning efficacy in vitro, various compositions or solutions of the invention were subjected to treatment as next described. Four different lens types (PMMA, CAB, HEMA and SILICONE) were subjected to artificial soiling with (1) hairspray (protein base), (2) human plasma protein, (3) lipstick, (4) pencil wax ("grease pencil"). Physiologically soiled lenses of each type were also included. Prior to cleaning, each lens was examined under a stereoptic microscope (30X), and a soilent factor was determined (4=100% dirty, 0=100% clean). After the application of the artificial soilents, all lenses were judged to be 4 (100% dirty). The physiologically soiled lenses were judged to be in various degrees of dirtiness, ranging from 2 to 4. All lenses were then subjected to a specific cleaning ritual. One drop of solution of the invention was placed on the lens surfaces. The lens were then rubbed between the index finger and thumb. Each lens was then rinsed in tap water and a second drop of solution was applied to the lens. Each lens was then observed under the stereoptic microscope and its degree of dirtiness judged. The results may be seen in Tables 1–4, included herein. It was evident from the results that the test solutions quickly and effectively cleaned all common forms of soilent from the surface of all commonly used lenses in vitro.

For purposes of testing the cleaning efficacy in vivo, various compositions or solutions of the invention were subjected to the following application. The use of the one-step cleaning, wetting, disinfecting, hydrating solution as described herein was tested for six (6) months on one hundred patients. The contact lenses worn in this study included the soft lens type, CAB and silicone type materials.

TABLE 1

| LENS TYPE: CAB | | | | | |
|---|---|---|---|---|---|
| SOILENTS | LENS | BEFORE CLEANING | AFTER 1st CLEANING | AFTER 2nd CLEANING | AFTER 3rd CLEANING |
| Lipstick | 1 | 4 | 2 | 0 | |
| | 2 | 4 | 1 | 0 | |
| | 3 | 4 | 0 | | |
| | 4 | 4 | 2 | 0 | |
| Hairspray | 1 | 4 | 0 | | |
| | 2 | 4 | 0 | | |
| | 3 | 4 | 0 | | |
| | 4 | 4 | 0 | | |
| Wax Pencil | 1 | 4 | 0 | | |
| | 2 | 4 | 1 | 0 | |
| | 3 | 4 | 0 | | |
| | 4 | 4 | 0 | | |
| Serum Protein | 1 | 4 | 0 | | |
| | 2 | 4 | 0 | | |
| | 3 | 4 | 0 | | |
| | 4 | 4 | 0 | | |
| Physiological Soil | 1 | 3 | 0 | | |
| | 2 | 2 | 0 | | |
| | 3 | 4 | 0 | | |
| | 4 | 4 | 0 | | |

4 = 100% Dirty
0 = 100% Clean

TABLE 2

| LENS TYPE: PMMA | | | | | |
|---|---|---|---|---|---|
| SOILENTS | LENS | BEFORE CLEANING | AFTER 1st CLEANING | AFTER 2nd CLEANING | AFTER 3rd CLEANING |
| Lipstick | 1 | 4 | 1 | 0 | |
| | 2 | 4 | 0 | | |
| | 3 | 4 | 0 | | |
| | 4 | 1 | 0 | | |
| Hairspray | 1 | 4 | 0 | | |
| | 2 | 4 | 0 | | |
| | 3 | 4 | 0 | | |
| | 4 | 4 | 0 | | |
| Wax Pencil | 1 | 4 | 0 | | |
| | 2 | 4 | 0 | | |
| | 3 | 4 | 0 | | |
| | 4 | 4 | 1 | 0 | |

TABLE 2-continued

LENS TYPE: PMMA

| SOILENTS | LENS | BEFORE CLEANING | AFTER 1st CLEANING | AFTER 2nd CLEANING | AFTER 3rd CLEANING |
|---|---|---|---|---|---|
| Serum Protein | 1 | 4 | 0 | | |
| | 2 | 4 | 0 | | |
| | 3 | 4 | 0 | | |
| | 4 | 4 | 0 | | |
| Physiological | 1 | 4 | 0 | | |
| Soil | 2 | 3 | 0 | | |
| | 3 | 4 | 0 | | |
| | 4 | 4 | 0 | | |

4 = 100% Dirty
0 = 100% Clean

TABLE 3

LENS TYPE: HEMA

| SOILENTS | LENS | BEFORE CLEANING | AFTER 1st CLEANING | AFTER 2nd CLEANING | AFTER 3rd CLEANING |
|---|---|---|---|---|---|
| Lipstick | 1 | 4 | 0 | | |
| | 2 | 4 | 0 | | |
| | 3 | 4 | 0 | | |
| | 4 | 4 | 0 | | |
| Hairspray | 1 | 4 | 0 | | |
| | 2 | 4 | 0 | | |
| | 3 | 4 | 0 | | |
| | 4 | 4 | 0 | | |
| Wax Pencil | 1 | 4 | 0 | | |
| | 2 | 4 | 0 | | |
| | 3 | 4 | 0 | | |
| | 4 | 4 | 0 | | |
| Serum Protein | 1 | 4 | 0 | | |
| | 2 | 4 | 0 | | |
| | 3 | 4 | 0 | | |
| | 4 | 4 | 0 | | |
| Physiological | 1 | 4 | 0 | | |
| Soil | 2 | 3 | 0 | | |
| | 3 | 4 | 0 | | |
| | 4 | 2 | 0 | | |

4 = 100% Dirty
0 = 100% Clean

TABLE 4

LENS TYPE: SILICONE

| SOILENTS | LENS | BEFORE CLEANING | AFTER 1st CLEANING | AFTER 2nd CLEANING | AFTER 3rd CLEANING |
|---|---|---|---|---|---|
| Lipstick | 1 | 4 | 2 | 1 | 0 |
| | 2 | 4 | 1 | 0 | |
| | 3 | 4 | 2 | 0 | |
| | 4 | 4 | 1 | 0 | |
| Hairspray | 1 | 4 | 0 | | |
| | 2 | 4 | 0 | | |
| | 3 | 4 | 0 | | |
| | 4 | 4 | 0 | | |
| Wax Pencil | 1 | 4 | 2 | 0 | |
| | 2 | 4 | 1 | 0 | |
| | 3 | 4 | 1 | 0 | |
| | 4 | 4 | 1 | 0 | |
| Serum Protein | 1 | 4 | 0 | | |
| | 2 | 4 | 0 | | |
| | 3 | 4 | 0 | | |
| | 4 | 4 | 0 | | |
| Physiological | 1 | 4 | 0 | | |
| Soil | 2 | 3 | 0 | | |
| | 3 | 2 | 0 | | |
| | 4 | 4 | 0 | | |

4 = 100% Dirty
0 = 100% Clean

TABLE 5

SUMMARIZED RESULTS OF IN VIVO TESTING
(6 month Study - 100 Patients)

| PATIENT | TYPE OF LENS | REACTION (ALLERGIC)* | CLEANING ABILITY++ | INTEGRITY |
|---|---|---|---|---|
| 1 | Soft Lens | 4 | 0 | Complete |
| 2 | Soft Lens | 4 | 0 | Complete |

TABLE 5-continued

SUMMARIZED RESULTS OF IN VIVO TESTING
(6 month Study - 100 Patients)

| PATIENT | TYPE OF LENS | REACTION (ALLERGIC)* | CLEANING ABILITY++ | INTEGRITY |
|---|---|---|---|---|
| 3 | Soft Lens | 4 | 1 | Complete |
| 4 | Soft Lens | 4 | 0 | Complete |
| 5 | Silicone | 4 | 0 | Complete |
| 6 | Silicone | 4 | 0 | Complete |
| 7 | Silicone | 4 | 0 | Complete |
| 8 | CAB | 4 | 0 | Complete |
| 9 | CAB | 4 | 0 | Complete |
| 10 | CAB | 4 | 0 | Complete |

*Reaction:
0 = 100% Reaction
1 = 75% Reaction
2 = 50% Reaction
3 = 25% Reaction
4 = 0% Reaction ++Degree of Dirtiness:
0 = 0%
1 = 25%
2 = 50%
3 = 75%
4 = 100%

The results (summarized in Table 5, included herein) indicated that the one-step solution applied in vivo was effective in cleaning the contact lenses without showing any hyperallergic or physiological reaction to the patients themselves or to the ocular network. The determination of the above results was made in part by slit lamp microscopy (Thorpe).

For purposes of testing, the composition or solution of the invention is first fabricated as indicated above or in the examples as follow hereinbelow. It is filter-sterilized (Gelman 0.45μ) and an inoculum of $10^5$ orgs/ml is prepared. The organisms used are *Escherichia coli*, *Staphylococcus aureus*, *Pseudomonas aeruginosa* and *Candida albicans*.

In the composition of the invention, thimerosal is a principal microbiocidal agent being active against all of the aforesaid organisms. Cyclohexane by itself has some inhibitory effect on the organisms tested. Ethanol has some inhibitory effect on the organisms tested as does also a trace amount of chloroform.

Together, cyclohexane, ethyl acetate, ethanol, and/or chloroform in the indicated compositions and concentrations in saline have a surprisingly greater inhibitory effect than the sum of the individual components. This is believed due to the ability of the ethanol to dissolve fully the cyclohexane, chloroform and/or ethyl acetate and potentiate their anti-microbial activity. Thus, the combination provides a synergistic effect on the kill-rate of the microorganisms tested.

While thimerosal is active against all of the tested organisms, it is least protective when tested against *Staphylococcus aureus*. This has been demonstrated by various studies (Eriksen et al, 1972) as well as by our own experience.

The total test solution or composition, when tested against *S. aureus* in particular, exhibited a kill-rate greater than that of concentrations of thimerosal and saline from 1.5 to 2.5 times the concentration used in the composition of the invention and in considerably less time. Past studies have indicated that the addition of other ingredients either had detrimental effects or no effect at all on the microbiocidal activity of the solution.

It appears thus that the additional ingredients of the composition of the invention have a novel effect of creating synergy in that they cause a kill-rate substantially greater than that caused by any single ingredient tested separately. To be more specific, the results have demonstrated that the combined solution with 0.004% thimerosal provides a four-hour or less asceptizing after an initial concentration of $10^5$ orgs/ml. Prior to this, 0.007% thimerosal was considered minimum to achieve sterilization within six hours while 0.01% thimerosal was needed for a four-hour kill time.

Figure 1:
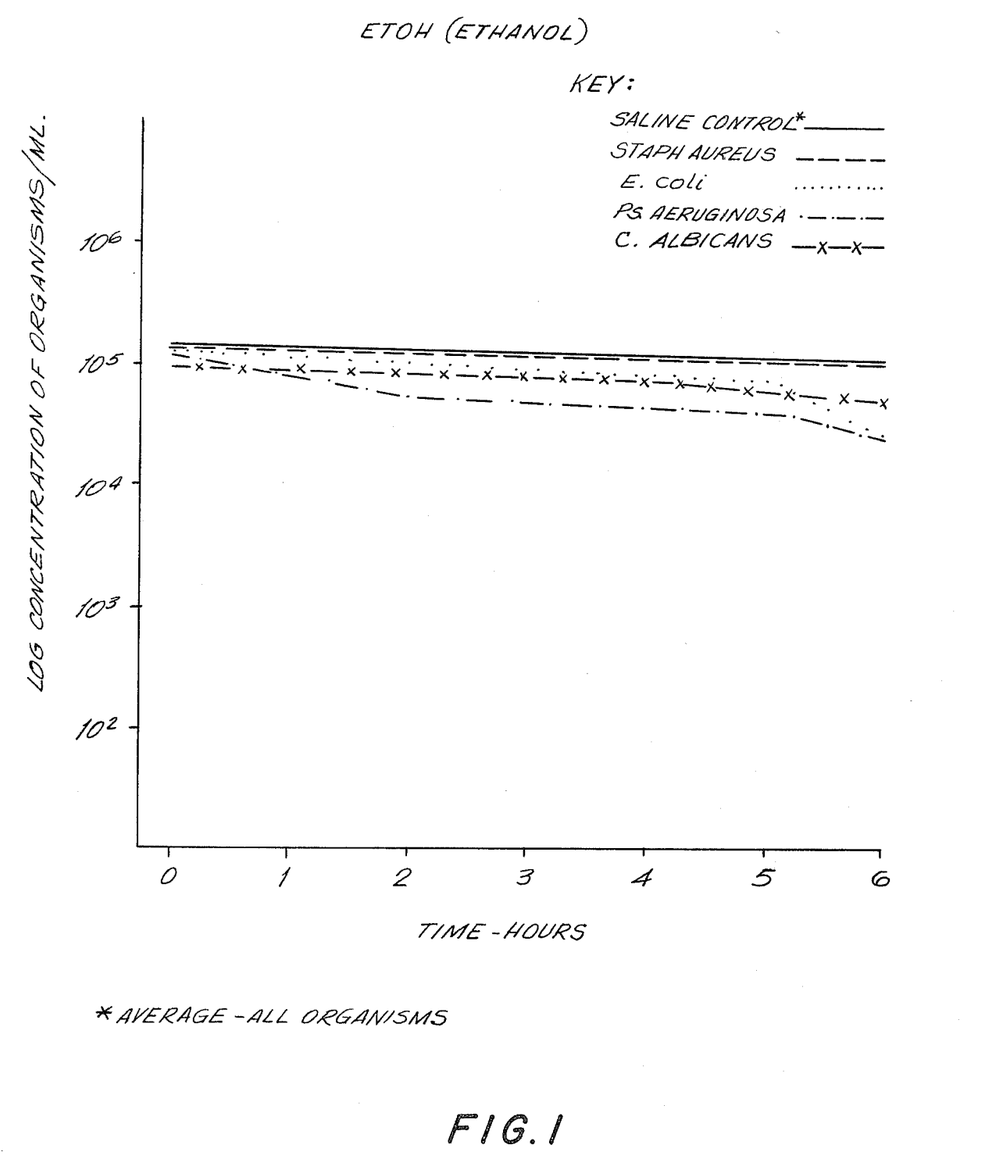
FIG. 1 is a chart illustrating the effectiveness of ethanol in the killing of various microorganisms.

FIGS. 1–5 indicate more clearly the dramatic synergistic effect of the ingredients tested which are considered to have anti-microbial activity. In FIG. 1, for example, it is seen that ethanol has little effect on the various microorganisms, including *S. aureus, E. coli, Ps. aeruginosa*, and *C. albicans*, as shown by the curves thereof relative to the saline control over a six-hour period. The level of the microorganisms appeared to remain at a count of $10^5$ organisms per ml.

Figure 2:
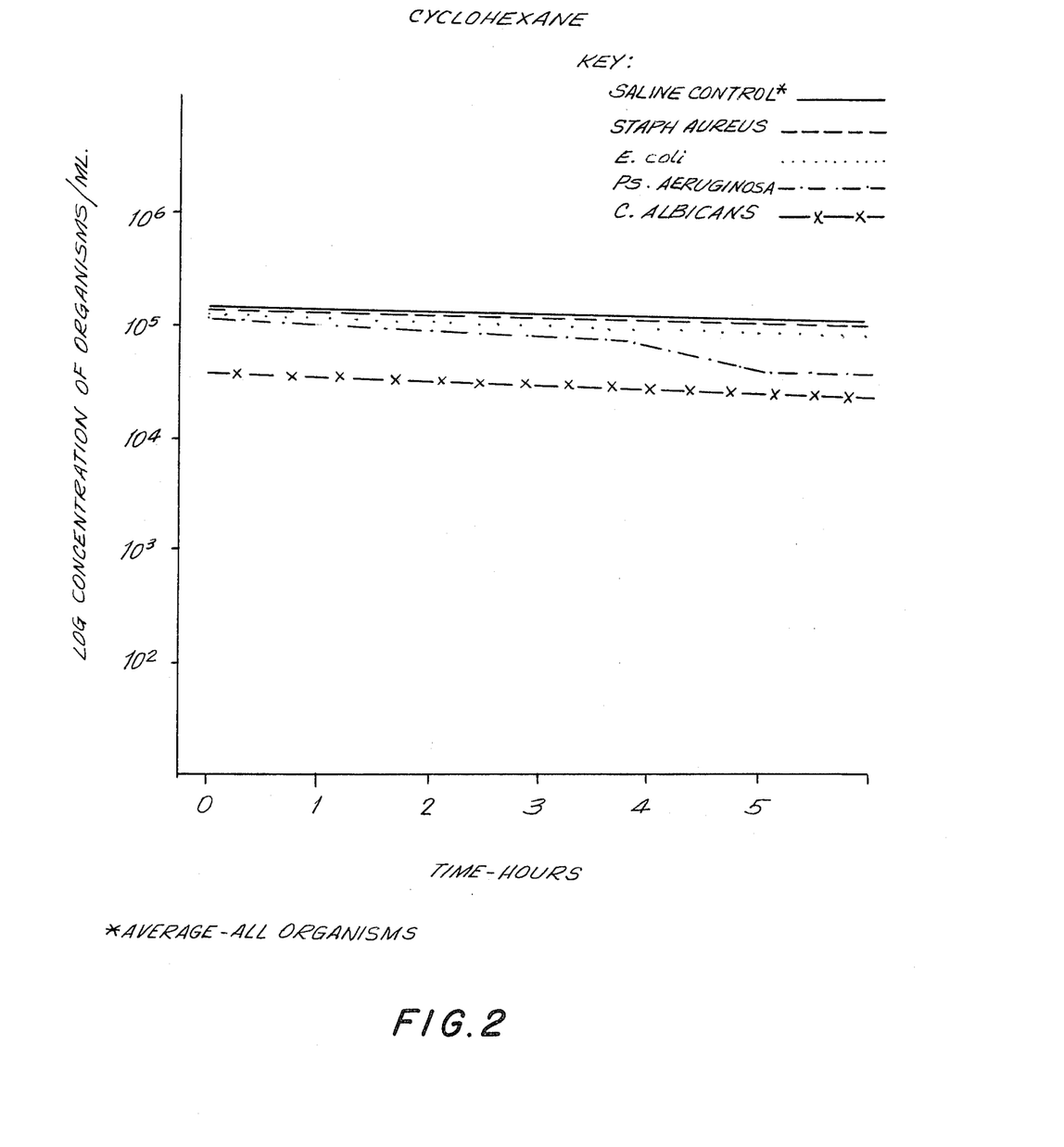
FIG. 2 is a chart corresponding to FIG. 1 showing the effectiveness of cyclohexane by itself.

FIG. 2 illustrates that cyclohexane alone has little effect on all of the aforesaid microorganisms.

Figure 3:
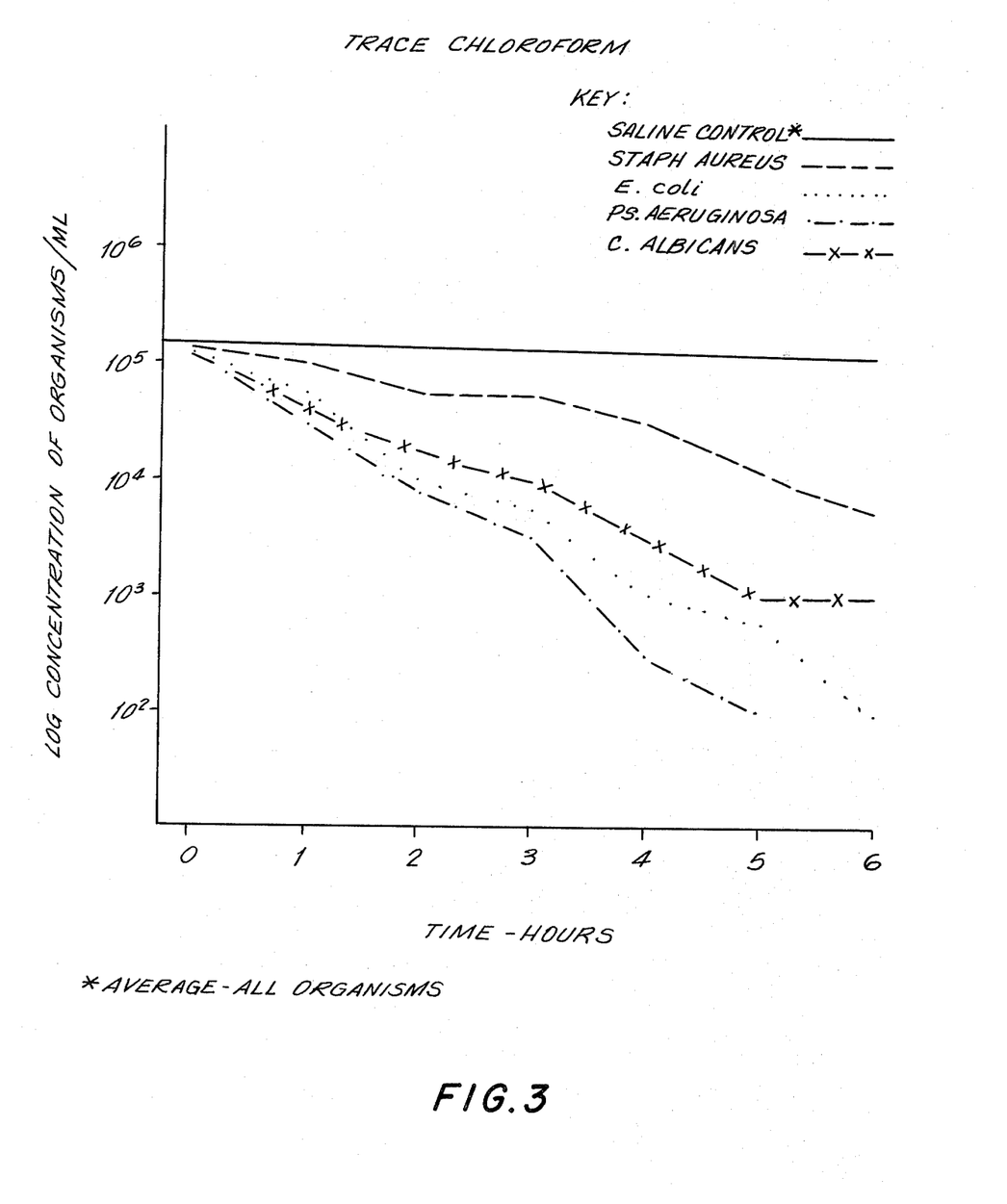
FIG. 3 is a chart corresponding to FIGS. 1 and 2 showing the effectiveness of chloroform by itself.

FIG. 3 illustrates that chloroform alone also has an effect on all of the microorganisms tested.

Figure 4:
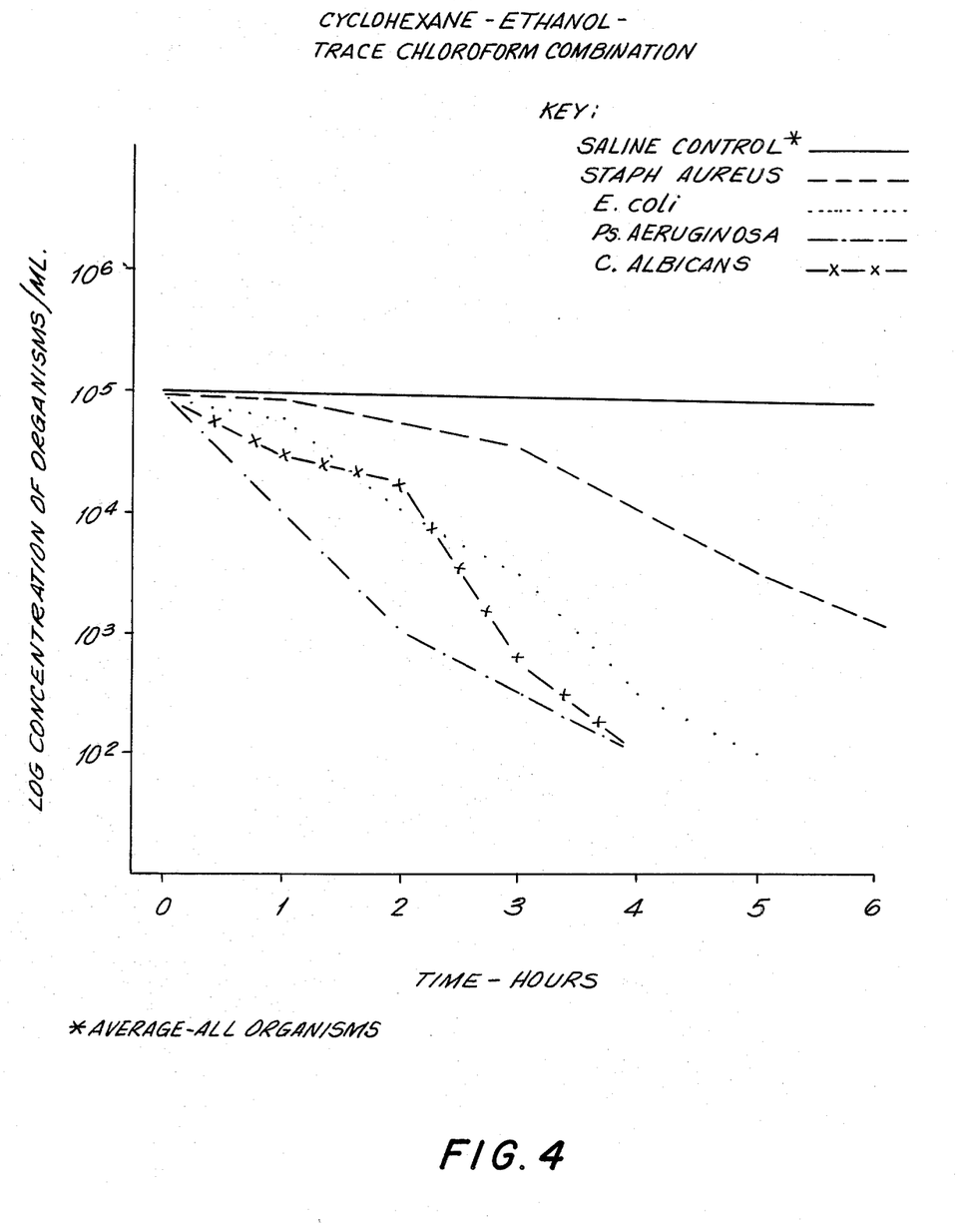
FIG. 4 is a chart corresponding to FIGS. 1, 2, and 3 showing the effectiveness of the cyclohexane, alcohol, trace chloroform and revealing the synergistic activity therebetween.

FIG. 4 shows the effect of combining ethanol, cyclohexane, and trace amounts of chloroform and thereby demonstrates clearly the synergistic effect between alcohol and the non-polar solvents. Herein it becomes obvious that a greatly enhanced effect is achieved against all of the microorganisms including not only *E. coli, Ps. aeruginosa*, and *C. albicans*, but against *S. aureus* as well. Thus, in a six-hour period, even the Staphylococcus is reduced to the amount of $10^3$ microorganisms per milliliter or less (tests on $10^6$ orgs/ml have been found to show the same or similar results).

Figure 5:
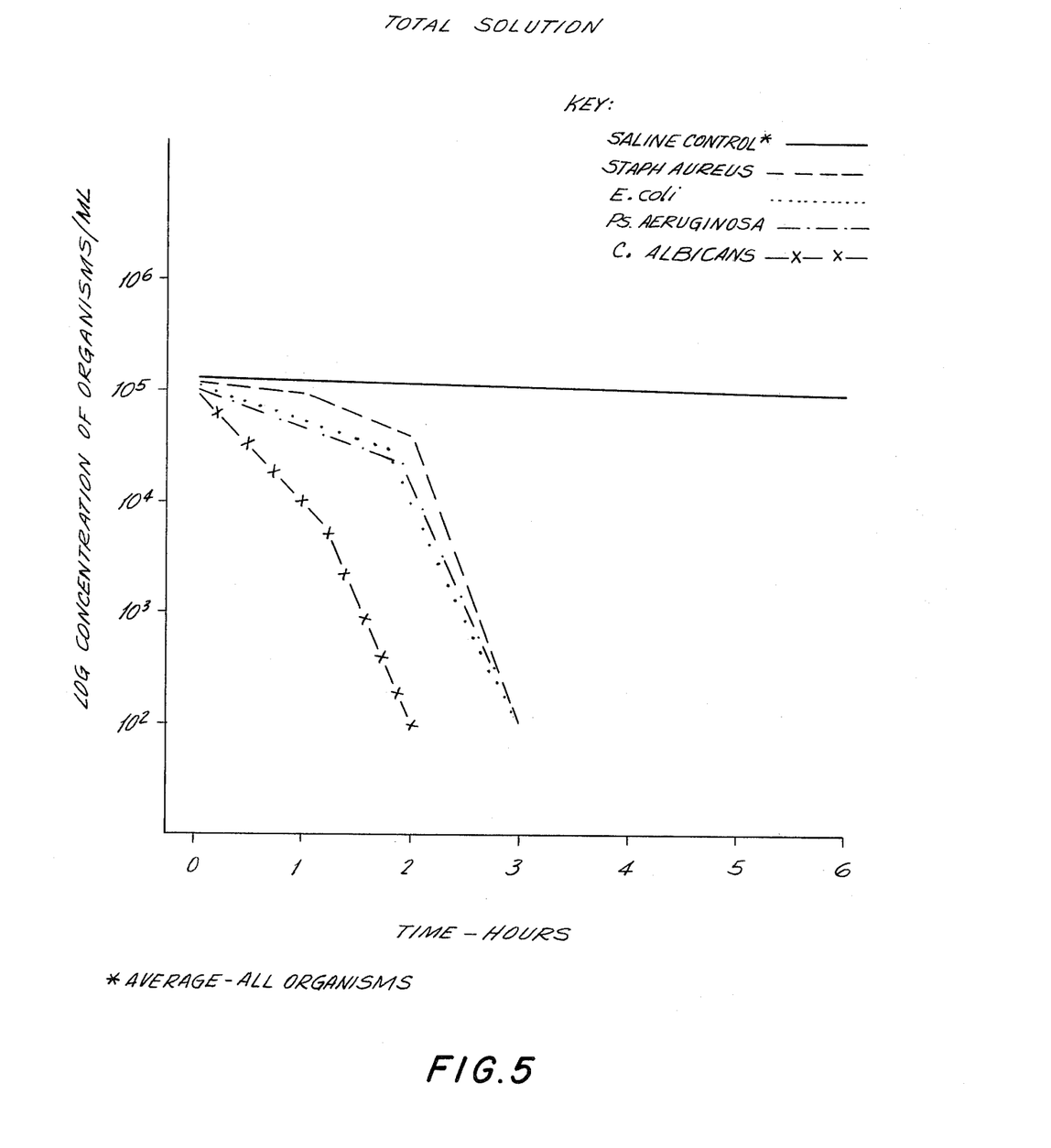
FIG. 5 is a chart corresponding to FIGS. 1-3 showing the effectiveness of a complete composition prepared in accordance with the invention, including cyclohexane, an alcohol and a trace amount of chloroform.

The results of the complete solution as shown in FIG. 5 show an even greater effect inasmuch as a solution of this type indicated above causes all of the microorganisms to be reduced to a minimum recoverable amount in approximately a 2–3 hour period. This result is substantially greater than that achievable with known solutions or compositions of the prior art.

Additional examples of the compositions of the invention are given below:

EXAMPLE 1

| | |
|---|---|
| Cyclohexane | 0.2% v/v |
| Octylphenoxypolyethoxyethanol | 0.001% w/v |
| Thimerosal | 0.004% w/v |
| Polyvinyl alcohol | 1.00% w/v |
| Ethanol | 1.00% w/v |
| Ethyl acetate | 0.001% v/v |
| NaCl | 0.9% w/v |
| Distilled water, QS | 100.00% |

EXAMPLE 2

| | |
|---|---|
| Cyclohexane | 0.1% v/v |
| Octylphenoxypolyethoxyethanol | 0.01% w/v |
| Phenylethylalcohol | 0.2% v/v |
| Polyvinyl alcohol | 1.0% w/v |
| Ethanol | 1.5% v/v |
| Chloroform | 0.0025% v/v |
| NaCl | 0.9% w/v |
| Distilled water, QS | 100.00% |

EXAMPLE 3

| | |
|---|---|
| Cyclohexane | 1.0% v/v |
| Dioctylsulfosuccinate | 0.01% w/v |
| Thimerosal | 0.005% w/v |
| Polyvinyl alcohol | 1.0% w/v |
| Ethanol | 2.0% v/v |
| Ethyl acetate | 0.005% v/v |
| NaCl | 0.9% w/v |
| Distilled water, QS | 100.00% |

EXAMPLE 4

| | |
|---|---|
| Cyclohexane | 0.005% v/v |

EXAMPLE 4-continued

| | | |
|---|---|---|
| Polyoxyethylene sorbitan monolaurate | 2.0% | w/v |
| Thimerosal | 0.005% | w/v |
| Polyvinyl alcohol | 0.85% | w/v |
| Ethanol | 1.75% | w/v |
| Chloroform | 0.1% | v/v |
| NaCl | 0.25% | v/v |
| KCl | 0.65% | w/v |
| Distilled water, QS | 100.00% | |

EXAMPLE 5

| | | |
|---|---|---|
| Cyclohexane | 0.07% | v/v |
| Octylphenoxypolyethoxyethanol | 3.0% | w/v |
| Chlorobutanol | 0.5% | v/v |
| Polyvinyl alcohol | 2.5% | w/v |
| Isopropanol | 3.0% | v/v |
| Ethyl acetate | 0.075% | v/v |
| NaCl | 0.9% | w/v |
| Distilled water, QS | 100.00% | |

EXAMPLE 6

| | | |
|---|---|---|
| Cyclohexane | 0.3% | v/v |
| Polyethylene stearate | 3.0% | w/v |
| Sorbic acid | 0.1% | w/v |
| Polyvinyl alcohol | 2.0% | w/v |
| Ethanol | 3.0% | v/v |
| Chloroform | 0.01% | v/v |
| NaCl | 1.0% | w/v |
| Distilled water, QS | 100.00% | |

EXAMPLE 7

| | | |
|---|---|---|
| Cyclohexane | 1.0% | v/v |
| Fatty alcohol ethoxylate (LUBROL-WX) | 0.01% | w/v |
| Phenylethylalcohol | 0.25% | v/v |
| Polyvinyl alcohol | 1.0% | w/v |
| Ethanol | 1.0% | v/v |
| Ethyl acetate | 0.005% | v/v |
| NaCl | 0.9% | w/v |
| Distilled water, QS | 100.00% | |

EXAMPLE 8

| | | |
|---|---|---|
| Cyclohexane | 0.7% | v/v |
| Fatty alcohol ethoxylate (LUBROL-WX) | 0.01% | w/v |
| Thimerosal | 0.007% | w/v |
| Polyvinyl alcohol | 0.75% | w/v |
| Ethanol | 1.5% | v/v |
| Chloroform | 0.002% | v/v |
| NaCl | 0.85% | w/v |
| Distilled water, QS | 100.00% | |

EXAMPLE 9

| | | |
|---|---|---|
| Cyclohexane | 0.06% | v/v |
| Polyethylene stearate | 0.01% | w/v |
| Chlorobutanol | 0.02% | v/v |
| Polyvinyl alcohol | 1.5% | w/v |
| Isopropanol | 1.5% | v/v |
| Ethyl acetate | 0.004% | v/v |
| NaCl | 0.9% | w/v |
| Distilled water, QS | 100.00% | |

EXAMPLE 10

| | | |
|---|---|---|
| Ethyl acetate | 0.05% | v/v |
| Octylphenoxypolyethoxyethanol | 0.001% | w/v |
| Thimerosal | 0.004% | w/v |
| Polyvinylalcohol | 1.00% | w/v |
| Ethanol | 1.00% | v/v |
| Sodium chloride | 0.9% | w/v |
| Distilled water, QS | 100.00% | |

EXAMPLE 11

| | | |
|---|---|---|
| Cyclohexane | 0.1% | v/v |
| Ethyl acetate | 0.001% | v/v |
| Octylphenoxypolyethoxyethanol | 0.01% | w/v |
| Chlorhexidine gluconate | 0.001% | v/v |
| Sodium edetate | 0.1% | w/v |
| Polyvinyl alcohol | 0.5% | w/v |
| Ethanol | 1.5% | v/v |
| Distilled water, QS | 100.00% | |

EXAMPLE 12

| | | |
|---|---|---|
| Ethyl acetate | 0.005% | v/v |
| Dioctylsulfosuccinate | 0.01% | w/v |
| Thimerosal | 0.005% | w/v |
| Sodium edetate | 0.05% | w/v |
| Polyvinyl alcohol | 1.0% | w/v |
| Ethanol | 2.0% | v/v |
| Sodium chloride | 0.7% | w/v |
| Distilled water, QS | 100.00% | |

EXAMPLE 13

| | | |
|---|---|---|
| Cyclohexane | 0.005% | v/v |
| Ethyl acetate | 0.1% | v/v |
| Polyoxyethylene sorbitan monolaurate | 2.0% | w/v |
| Thimerosal | 0.005% | w/v |
| Polyvinylalcohol | 0.85% | w/v |
| Isopropanol | 1.0% | v/v |
| Sodium chloride | 0.25% | w/v |
| Potassium chloride | 0.65% | w/v |
| Distilled water, QS | 100.00% | |

EXAMPLE 14

| | | |
|---|---|---|
| Ethyl acetate | 0.075% | v/v |
| Octylphenoxypolyethoxyethanol | 3.0% | w/v |
| Benzalkonium chloride | 0.001% | w/v |
| Sodium edetate | 0.1% | w/v |
| Polyvinylalcohol | 2.5% | w/v |
| Ethanol | 0.5% | v/v |
| Sodium chloride | 0.8% | w/v |
| Distilled water, QS | 100.00% | |

EXAMPLE 15

| | | |
|---|---|---|
| Cyclohexane | 0.3% | v/v |
| Ethyl acetate | 0.2% | v/v |
| Polyethylene stearate | 3.0% | w/v |
| Thimerosal | 0.004% | w/v |
| Sodium edetate | 0.1% | w/v |
| Polyvinyl alcohol | 2.0% | w/v |
| Ethanol | 2.0% | v/v |
| Potassium chloride | 0.9% | w/v |
| Distilled water, QS | 100.00% | |

EXAMPLE 16

| | | |
|---|---|---|
| Ethyl acetate | 0.001% | v/v |
| Fatty alcohol ethoxylate (LUBROL-WX) | 0.01% | w/v |
| Chlorobutanol | 0.5% | v/v |
| Polyvinylalcohol | 1.0% | w/v |
| Ethanol | 1.0% | v/v |
| Sodium chloride | 0.9% | w/v |
| Distilled water, QS | 100.00% | |

EXAMPLE 17

| | | |
|---|---|---|
| Cyclohexane | 0.3% | v/v |
| Ethyl acetate | 0.01% | v/v |
| Octylphenoxypolyethoxyethanol | 0.005% | w/v |
| Thimerosal | 0.006% | w/v |
| Polyvinylalcohol | 0.75% | w/v |
| Ethanol | 1.5% | v/v |
| Sodium borate | 0.8% | w/v |

EXAMPLE 17-continued

| | |
|---|---|
| Distilled water, QS | 100.00% |

EXAMPLE 18

| | |
|---|---|
| Ethyl acetate | 0.1% v/v |
| Polyethylene stearate | 0.01% w/v |
| Thimerosal | 0.001% w/v |
| Benzalkonium chloride | 0.001% w/v |
| Sodium edetate | 0.1% w/v |
| Polyvinylalcohol | 1.5% w/v |
| Isopropanol | 1.5% v/v |
| Sodium chloride | 0.7% w/v |
| Distilled water, QS | 100.00% |

EXAMPLE 19

| | |
|---|---|
| Ethyl acetate | 0.02% v/v |
| Cyclohexane | 0.1% v/v |
| Octylphenoxypolyethoxyethanol | 0.01% w/v |
| Chlorhexidine | 0.001% w/v |
| Polyvinyl alcohol | 2.0% w/v |
| Isopropanol | 0.5% v/v |
| Potassium chloride | 0.6% w/v |
| Sodium chloride | 0.2% w/v |
| Distilled water, QS | 100.00% |

EXAMPLE 20

| | |
|---|---|
| Ethyl acetate | 0.025% v/v |
| Dioctylsulfosuccinate | 0.1% w/v |
| Thimerosal | 0.002% w/v |
| Sodium edetate | 0.1% w/v |
| Polyvinyl alcohol | 0.5% w/v |
| Ethanol | 0.5% v/v |
| Sodium chloride | 1.0% w/v |
| Distilled water, QS | 100.00% |

EXAMPLE 21

| | |
|---|---|
| Ethyl acetate | 0.01% v/v |
| Octylphenoxypolyethoxyethanol | 0.001% w/v |
| Thimerosal | 0.003% w/v |
| Sodium edetate | 0.1% w/v |
| Chlorhexidine gluconate | 0.0001% w/v |
| Polyvinylalcohol | 1.0% w/v |
| Ethanol | 0.75% v/v |
| Sodium chloride | 0.8% w/v |
| Distilled water, QS | 100.00% |

It will now become obvious to those skilled in the art that numerous modifications and variations can be made without departing from the scope and spirit of the invention as defined in the attached claims.

What is claimed is:

1. A composition suitable for cleaning lenses and adapted to provide for enhanced solubility of lipids and lipoproteins which comprises in aqueous solution 0.001 to 1.0% by volume of a non-polar solvent which is cyclohexane or ethyl acetate.

2. A composition as claimed in claim 1 which further comprises an additional organic solvent which is chloroform.

3. A composition as claimed in claim 2 wherein the additional organic solvent is present in an amount of 0.0001–0.01% by volume.

4. A composition as claimed in claim 3 which further comprises an alcohol selected from the group consisting of ethanol and isopropanol.

5. A composition as claimed in claim 4 wherein the non-polar solvent is a mixture of cyclohexane and ethyl acetate.

6. A composition as claimed in claim 4 wherein the alcohol is present in an amount of 0.1–10% by volume.

7. A composition as claimed in claim 4 which further comprises NaCl or KCl.

8. A composition as claimed in claim 4 wherein the aqueous solution consists of normal saline.

9. A composition as claimed in claim 8 wherein the saline is 0.85–0.95 weight percent of NaCl.

10. A composition as claimed in claim 7 which further comprises a surfactant.

11. A composition as claimed in claim 10 wherein the surfactant is a non-ionic surfactant present in an amount of about 0.0001–10% by weight.

12. A composition as claimed in claim 10 wherein the surfactant is a salt of a fatty acid.

13. A composition as claimed in claim 10 wherein the surfactnt is selected from the group consisting of octylphenoxypolyethoxyethanol, fatty alcohol ethoxylate, Polyethylene stearate and polyoxyethylene sorbitan monolaurate.

14. A composition as claimed in claim 7 which further comprises an antimicrobial agent.

15. A composition as claimed in claim 14 wherein the antimicrobial agent is thimerosal.

16. A composition as claimed in claim 15 wherein the thimerosal is present in an amount of about 0.0005–0.7% by weight.

17. A composition as claimed in claim 15 wherein the thimerosal is present in an amount of about 0.004% by weight.

18. A composition as claimed in claim 7 which further comprises a wetting agent selected from the group consisting of polyvinyl alcohol, methylcellulose, hydroxypropylmethycellulose, dextran and polyethyleneglycol homopolymers.

19. A composition as claimed in claim 18 wherein the wetting agent is present in the amount of about 0.05–10% by weight.

20. A composition as claimed in claim 7 which further comprises a buffer to adjust the pH range to about 5–10.

21. A composition as claimed in claim 20 wherein the buffer is a sodium or potassium phosphate, citrate or borate.

22. A composition as claimed in claim 5 wherein the composition consists essentially of:
   0.001–1.0% by volume of said cyclohexane or ethyl acetate
   0.1–10% by volume of said ethanol
   0.0001–0.01% by volume of said chloroform
   q.s. to 100% by volume of normal saline
   0.0001–10% by weight of a physiologically acceptable surfactant
   0.05–10% by weight of a physiologically acceptable wetting agent selected from the group consising of polyvinyl alcohol, methylcellulose, hydroxypropylmethycellulose, dextran and polyethyleneglycol homopolymers,
   0.05–1.0% by weight of a buffer
   0.0005–0.7% by weight of thimerosal.

23. A method for the cleaning of a contact lens comprising applying to the lens a composition which includes in aqueous solution 0.001 to 1.0% by volume of a non-polar solvent which is cyclohexane or ethyl acetate.

24. A method as claimed in claim 23 wherein the non-polar solvent is present in an amount of about 0.02–0.3% by volume.

25. A method as claimed in claim 23 wherein the composition includes at least one alcohol selected from the group consisting of ethanol and isopropanol.

26. A method as claimed in claim 25 wherein the alcohol is ethanol.

27. A method as claimed in claim 26 wherein the composition further includes an additional organic solvent which is chloroform.

28. A method as claimed in claim 27 wherein the chloroform is present in an amount of about 0.0001–0.01% by volume.

29. A method as claimed in claim 28 wherein the composition further includes NaCl or KCl.

30. A method as claimed in claim 28 wherein the non-polar solvent is a mixture of cyclohexane and ethyl acetate.

31. A method as claimed in claim 28 wherein the aqueous solution consists of normal saline and the saline is 0.85–0.95 weight percent of NaCl.

32. A method as claimed in claim 28 wherein the composition further includes a wetting agent selected from the group consisting of polyvinyl alcohol, methylcellulose, hydroxypropylmethycellulose, dextran and polyethylene glycol homopolymers.

33. A method as claimed in claim 32 wherein the wetting agent is present in the amount of about 0.05–10% by weight.

34. A method as claimed in claim 33 wherein the wetting agent is polyvinyl alcohol.

35. A method as claimed in claim 28 wherein the composition further includes about 0.0005–0.7% by weight of thimerosal.

36. A method as claimed in claim 35 wherein the thimerosal is present in an amount of about 0.004% by weight.

37. A method as claimed in claim 28 wherein the composition further includes a surfactant.

38. A method as claimed in claim 37 wherein the surfactant is a non-ionic surfactant present in an amount of about 0.0001–10% by weight.

39. A method as claimed in claim 38 wherein the surfactant is octylphenoxypolyethoxyethanol.

40. A method as claimed in claim 38 wherein the surfactant is a salt of a fatty acid.

41. A method as claimed in claim 28 wherein the composition further includes a buffer to adjust the pH range to about 7.1–7.4.

42. A method as claimed in claim 27 wherein the composition consists essentially of:
  0.001–1.0% by volume of said cyclohexane or ethyl acetate
  0.1–10% by volume of said ethanol
  0.0001–0.01% by volume of said chloroform
  q.s. to 100% by volume of normal saline
  0.0001–10% by weight of a physiologically acceptable surfactant
  0.05–10% by weight of a physiologically acceptable wetting agent selected from the group consisting of polyvinyl alcohol, methylcellulose, hydroxypropylmethycellulose, dextran and polyethyleneglycol homopolymers,
  0.05–1.0% by weight of a buffer
  0.0005–0.7% by weight of thimerosal.

43. A method as claimed in claim 42 wherein the surfactant is selected from the group consisting of octylphenoxypolyethoxyethanol, dioctylsulfosuccinate, fatty alcohol ethoxylate, polyethylene stearate and polyoxyethylene sorbitan monolaurate.

* * * * *